US006363966B1

United States Patent
Browne

(10) Patent No.: US 6,363,966 B1
(45) Date of Patent: Apr. 2, 2002

(54) STREAM SWITCHING SYSTEM

(75) Inventor: Edward M. Browne, Houston, TX (US)

(73) Assignee: Daniel Industries, Inc., Houston, TX (US)

( * ) Notice: Subject to any disclaimer, the term of this patent is extended or adjusted under 35 U.S.C. 154(b) by 0 days.

(21) Appl. No.: 09/538,254

(22) Filed: Mar. 30, 2000

Related U.S. Application Data

(60) Provisional application No. 60/141,357, filed on Jun. 28, 1999.

(51) Int. Cl.[7] ............................................. F16K 11/20
(52) U.S. Cl. ...................................... 137/597; 137/606
(58) Field of Search ............................... 137/597, 606, 137/607

(56) References Cited

U.S. PATENT DOCUMENTS

| | | | | |
|---|---|---|---|---|
| 4,304,257 A | * | 12/1981 | Webster | 137/559 |
| 4,353,243 A | * | 10/1982 | Martin | 73/863.71 |
| 4,703,913 A | * | 11/1987 | Hunkapiller | 251/61.1 |
| 5,123,443 A | * | 6/1992 | Garrison | 137/565 |
| 5,201,219 A | | 4/1993 | Bandurski et al. | 73/153 |
| 5,325,889 A | * | 7/1994 | Paul et al. | 137/594 |
| 5,368,062 A | * | 11/1994 | Okumura et al. | 137/240 |
| 5,653,259 A | | 8/1997 | Ramstad | 137/606 |

FOREIGN PATENT DOCUMENTS

| | | | |
|---|---|---|---|
| EP | 0 583 166 A2 | 2/1994 | F16K/3/00 |
| FR | 2 664 671 | 1/1992 | F16K/11/02 |
| WO | WO 97/19283 | 5/1997 | F16K/11/24 |

OTHER PUBLICATIONS

International Serach Report for International Application No. PCT/US00/15833 dated Oct. 9, 2000; (6 p.).

\* cited by examiner

Primary Examiner—Stephen M. Hepperle
(74) Attorney, Agent, or Firm—Conley, Rose Tayon, P.C.

(57) ABSTRACT

A novel double block and double bleed stream switching system includes a common stream path for a multitude of fluid streams from, for example, a process pipeline. The common stream path includes a blocking port and a bleed port, and connects to at least one sample shut off. Preferably, the common stream path and sample shut off are shallow channels machined in a multi-layered block, with integrated pistons and ports controlling the flow from each stream and through the stream switching system.

39 Claims, 4 Drawing Sheets

STREAM SWITCHING SYSTEM

CROSS-REFERENCE TO RELATED APPLICATIONS

This application claims priority to provisional application 60/141,357 filed Jun. 28, 1999.

STATEMENT REGARDING FEDERALLY SPONSORED RESEARCH OR DEVELOPMENT

Not Applicable.

BACKGROUND OF THE INVENTION

It is often very important to know what fluids are flowing through a conduit such as a pipeline. For example, a buyer and seller of gas may agree upon a price for the fluid flowing through a process pipeline based upon the content of the fluid stream. Thus, the fluid content must be measured. Where multiple pipelines are positioned near one another, it may be economical to use a single meter or measurement device to monitor all of the fluid flows. The device used to extract and deliver the fluid to the measurement device is traditionally referred to as a sampling system.

FIG. 1 includes a stream sampling system ("sampling system") 100. Although only a single pipeline is shown, it is to be understood that multiple pipelines may be present. Sampling system 100 includes a sample point attached to pipeline 110, an analyzer 130, and tubing 120 from the sample point to the analyzer 130. Analyzer 130 may include a stream switching system 140 and gas chromatograph 150. In operation, fluid flow through a process pipeline 110. The sample point (preferably a probe) obtains a sample of fluid and delivers it to analyzer 130 via tubing 120. Analyzer 130 measures the content of the fluid sample and either returns the sample to the pipeline or vents the sample to the ambient environment.

One problem with such a layout is the large distance from the analyzer 130 to the pipeline 110, which creates a large "dead volume" of fluid. Increased dead volume results in undue mixing of consecutive fluid samples. This mixing of fluid samples results in "carry over" between samples for gas chromatograph analysis. Carry over is undesirable because accurate analysis requires that the analysis is representative of the fluid in the process pipeline. Since the volume of transport tubing and stream sampling components must be flushed a minimum of ten times to ensure a representative sample, the "dead volume" results in significant lag time between sample analysis. Therefore, upon a sampling of fluid from the pipeline 110, the "dead volume" of fluid must be vented or otherwise disposed of before the new sample can be measured at the analyzer 130. Further, although the magnitude of the "dead volume" could be reduced by placing the analyzer 130 closer to the sample point 110, regulations and safety concerns mandate a minimum 50 feet distance between them. If placed closer than 50 feet from the pipeline 110, the analyzer 130 must be contained in an expensive explosion-proof housing.

FIG. 2 includes a stream switching system 140 attached to an analyzer oven 250 that is part of gas chromatograph 150. Three pipes or tubes 210, 220, 230 attach to switching system 140, and correspond to first, second and third flow paths. The first pipe or tube 210 connects to a first sample point 212 and carries a first sample of unknown composition from, for example, a process pipeline. Included along "stream 1" are pressure regulator 214 and pressure gage 215, shut-off valve 216, particulate filter 217, and a first stream switching valve 218. Second pipe or tube 220 connects to a second sample point 222 and carries second gas stream of unknown composition. Included along "stream 2" are pressure regulator 224 and pressure gage 225, shut-off valve 226, particulate filter 227, and a second stream switching valve 228. The third pipe or tube 230 connects to a third sample point 232 and a calibration sample of known composition. Included along the third path are pressure regulator 234 and pressure gage 235, shut-off valve 236, particulate filter 237, and a third switching valve 238. Third switching valve 238 connects not only to filter 237, through one port, but also to first and second switching valves 218, 228 through another. Yet another port of third switching valve 238 attaches to regulator 240 and flow meter 245. Flow meter 245 attaches through a relatively long tube to sample shut-off valve 255 housed in analyzer oven 250. Shut off valve 255 connects to a sample valve in the oven, and then connects to the vent 260. As can be appreciated, although only two streams of unknown fluids are shown, additional streams could be added by the use of a greater number of flow paths.

During operation, a gas chromatograph housed in analyzer oven 250 is calibrated using the calibration sample from sample point 232. The pressure and flow rate of this stream are maintained by pressure regulator 234, regulator 240 and flow meter 245. Because the composition of the calibration sample is known, it may be used to calibrate the gas chromatograph. The calibration sample flows through third switching valve 238, through the gas chromatograph 150 and out sample vent 260. If a measurement of the fluid at sample point 222 is desired, the gas along the second pipe is allowed to flow by actuation of second stream switching valve 228, through first stream switching valve 218, and through third stream switching valve 238. The third switching valve 238 is the only valve in the stream switching system that on its own can prevent or block the flow of fluid from all the sample points. Thus, this configuration is referred to as a "single block" stream switching system. One drawback of this design is that the fluid from sample point 222 flows through all of the first, second, and third switching valves prior to arrival at the gas chromatograph, and malfunction of only a single one of these switching valves prevents the measurement of a sample of fluid from stream 2.

If after the above-described measurement of stream 2, it is desired to measure the fluid from stream 1, the system must be purged of the previous fluid sample. Purging of the old fluid stream from the system prevents contamination between the streams. Thus, the stream switching system of FIG. 2 would switch from stream 2 to stream 1. At that time, adequate accuracy by the gas chromatograph has likely been assured if all the other necessary criteria have been met. Many refer to a configuration having a single sample vent as a "single bleed" stream switching system.

Thus, a "dead volume" of fluid in a stream switching system is a significant problem. Another problem encountered in a stream switching system is the reliability and maintenance of the system. Because an operator may visit a particular stream switching system only infrequently, the system should be accurate, reliable, as immune to breakdown as possible, and simple to repair when problems do occur. This highly sought after combination of features is not available with current stream switching systems. It would also be desirable to have a multi-use gas sampling system that can be rapidly reconfigured in the field, at a sampling site, or in a manufacturing facility for semi-custom application.

Another drawback in many prior systems is their difficulty in analyzing a complex fluids because of limitations in the associated gas chromatographs. It would be desirable if a stream switching system could be developed that could quickly transfer fluid sample to the analyzer. This drawback also reduces the usefulness of a stream sampling system.

A stream sampling system is needed that is faster, more reliable, more flexible, and more accurate than previous stream sampling systems. Ideally, such a stream sampling system could reduce the adverse effects of "dead volume." This ideal stream sampling system would also be less prone to breakdown than previous models, while providing much faster and more accurate measurements.

SUMMARY OF THE INVENTION

The invention features a stream switching system including a housing forming at least one common stream path. The common stream path of this housing includes an actuatable input port corresponding to a first fluid sample, an actuatable input port corresponding to a second fluid sample, and a first actuatable output port to direct the first and second fluid samples away from the common stream path portion. Each of these actuatable input and output ports is actuatable between an open and a closed position. The stream switching system may also include a first sample shut off portion in communication with the common stream path portion, the first sample shut off portion having a third input port and a second output port. At least one of these ports in the first sample shut off is actuatable. The common stream path may include another output, this being a bleed path. The housing may include one or more pistons, the first actuatable input allowing a flow of the first fluid sample through the first fluid sample input when the first piston is in a first position and not allowing a flow of the first fluid sample through the first fluid sample input when the first piston is in a second position. Associated solenoids may be attached to the housing. Preferably, the housing is made up of a plurality of layers, with each layer separated from an adjacent layer by one or more gas impermeable diaphragms. One or more layers may be easily reconfigured to modify operability. The common stream path portion may be a cavity formed between a pair of these layers.

Thus, the present invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Figure 1:
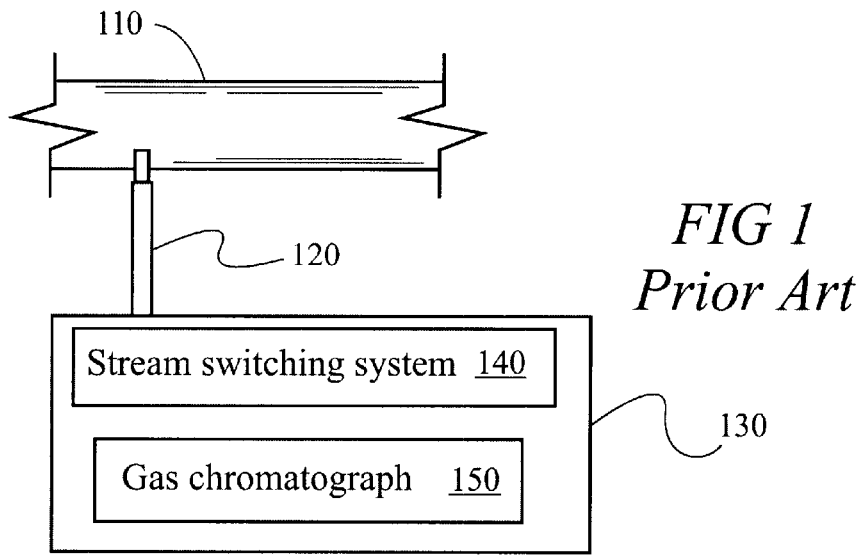
FIG. 1 is a prior art sample handling system.
Figure 2:
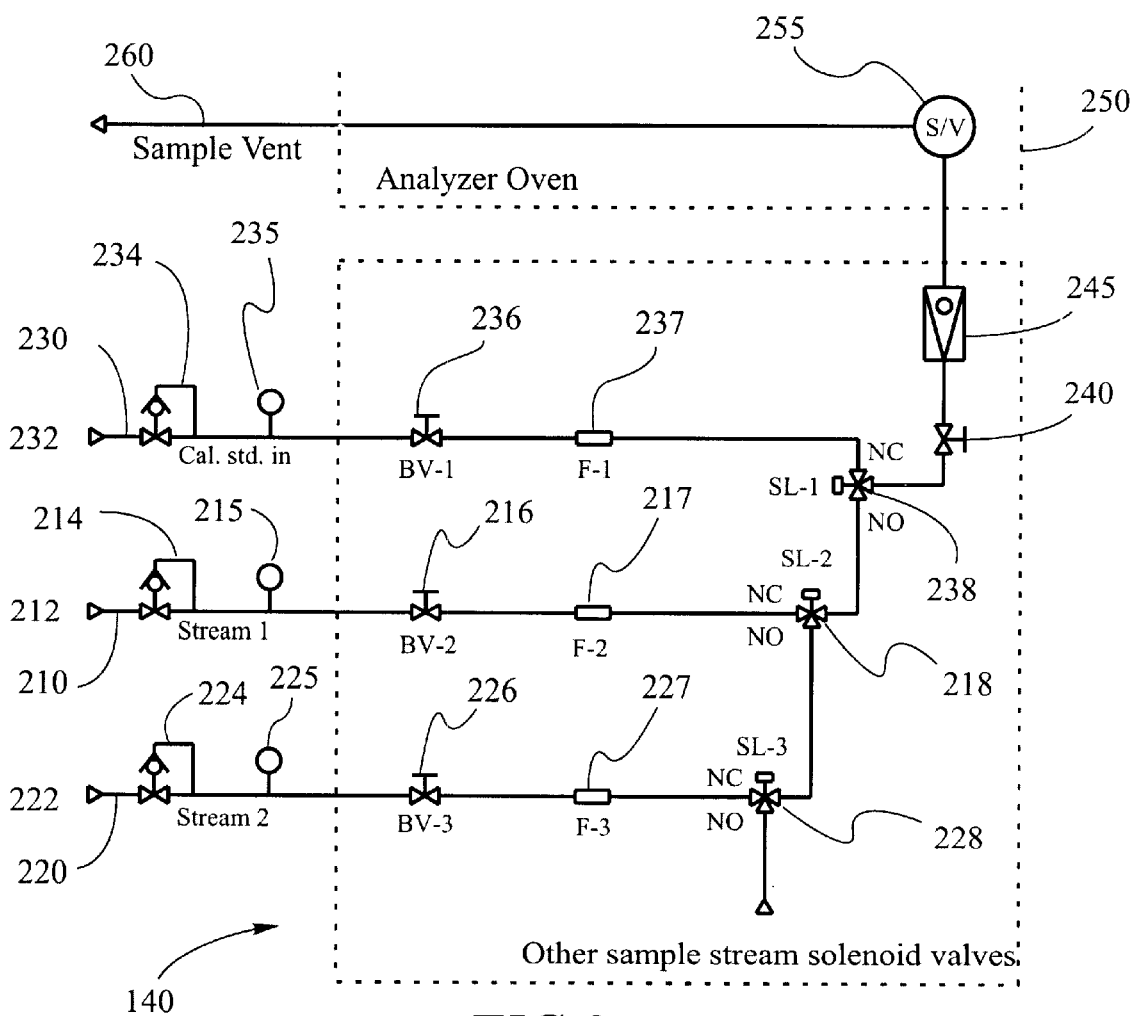
FIG. 2 is a prior art stream switching system.
Figure 3:
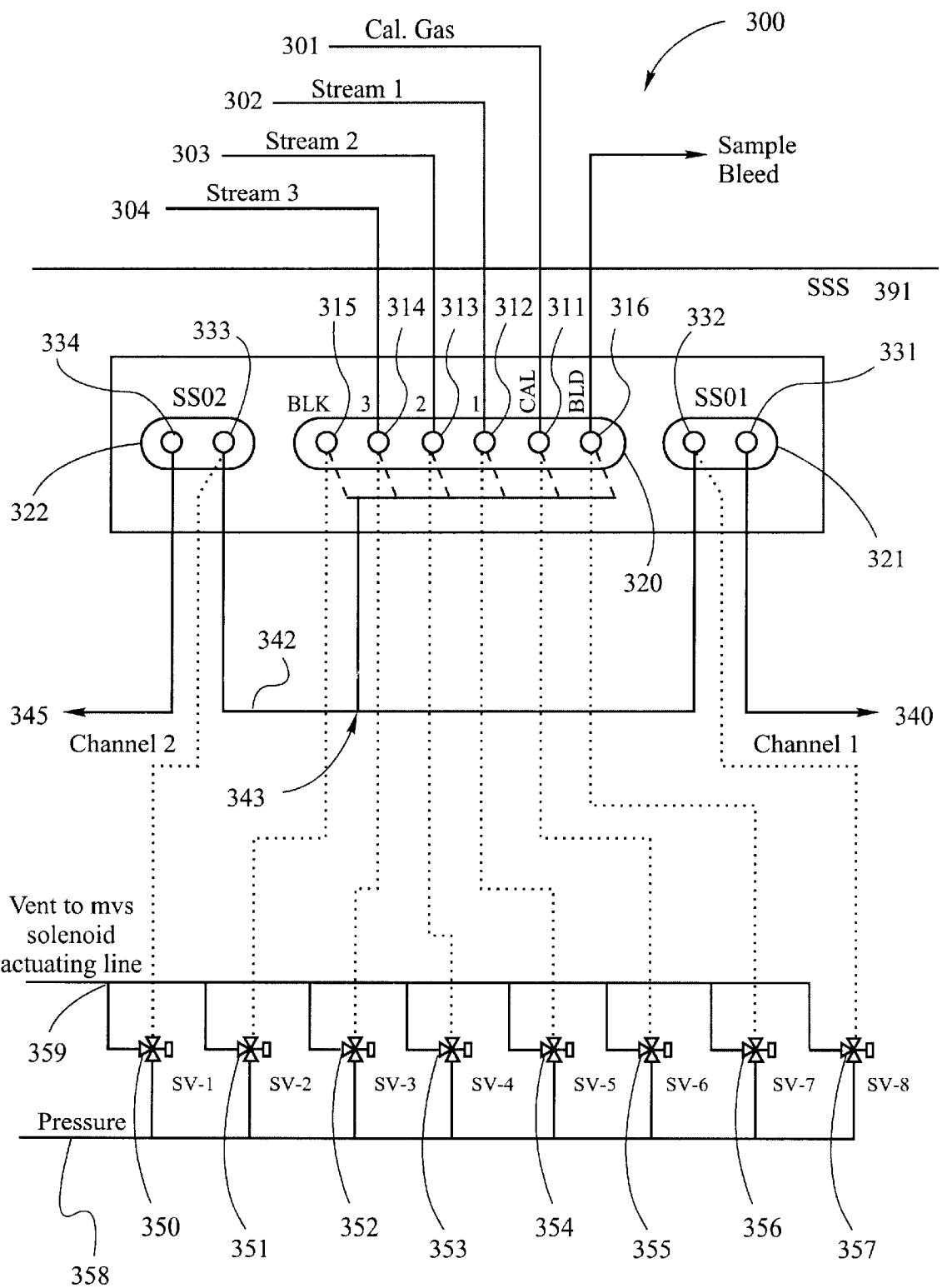
FIG. 3 is a schematic of a stream switching system according to an embodiment of the present invention.

FIG. 3 shows a "double block and double bleed" of one preferred embodiment of a stream switching system according to the invention. The stream switching system 300 includes four streams upstream of a stream handling portion 391. Four streams include a calibration sample 301, stream 1 302 corresponding to a first fluid sample, stream 2 303 corresponding to a second fluid sample, and stream 3 304 corresponding to a third fluid sample. It is to be understood that more or fewer ports can be included and that one or more separate stream switch systems could be included.

Streams 301–304 supply various fluid samples to the sample wetted portion, and connect respectively to actuatable calibration port 311 and actuatable stream ports 312–314. Actuatable ports 315–316 and 332–333, as well as ports 331 and 334, are also part of the sample wetted portion 391. Each actuatable port may be actuated into either an open or closed state as controlled by eight connected solenoids 350–357 (also labeled SV1–SV8) which correspond respectively to ports 311–316, 332–333. When a port is in an open state, fluid may pass freely through the port. When a port is in a closed state, fluid is prevented from flowing through that port. Also shown in FIG. 3 are solenoid pressure line 358 and solenoid vent line 359, as well as gas path 342 extending from port 315 to ports 333 and 332.

As explained further below, each actuatable stream port 312–314, as well as actuatable calibration port 311, is positioned in an area 320 that creates a common sample path. Also positioned in the common sample path 320 are an actuatable "blocking" port 315 and an actuatable "bleed" port 316. In addition, area 321 creates a first sample shut off that contains two "blocking" ports 332 and port 331. Area 322 creates a second sample shut off that contains two "blocking" ports 333 and port 334. As shown, ports 332 and 333 are actuatable, while ports 331 and 334 are not. It is to be understood, however, that all of these ports could be actuatable, or that ports 332 and 333 could be actuatable while ports 331 and 334 are not.

Two channels, channel 1 340 and channel 2 345, are output tubing that direct fluid sample away from the stream switching system. As used with reference to the invention, the term tubing is used in a general manner and includes other fluid transportation mediums such as piping. The channels connect to, for example, downstream gas chromatographs including valve, heating, and measurement devices. Each channel thus may be separately analyzed by a gas chromatograph. Each channel can also be used as a flow path to "bleed" the system when switching from sample point to sample point.

As can also be appreciated, first and second sample shut offs correspond to first and second channels 340, 345. Consequently each channel is associated with two solenoids 350 and 357, either one of which can be actuated to prevent the flow of any fluid through the channel. It can be appreciated that the use of a solenoid to prevent the flow of fluid is not absolutely necessary, and any suitable mechanical or electrical gas flow actuation switch may be used. In the illustrated embodiment, the flow of fluid through channel 1 may be prevented by closing either actuatable blocking port 315 or actuatable port 332 in the first sample shut off. Similarly, the flow of fluid through channel 2 may be prevented by closing either actuatable blocking port 315 or the actuatable port 333 in the second sample shut off. Thus, because the flow of fluid may be prevented through a channel at either of two locations, this is a "double block" design. In addition, the system may be bled through sample bleed port 316. Thus, because the system may be bled either through a channel or through the sample bleed port 316 the embodiment is a "double bleed" design.

Figure 4:
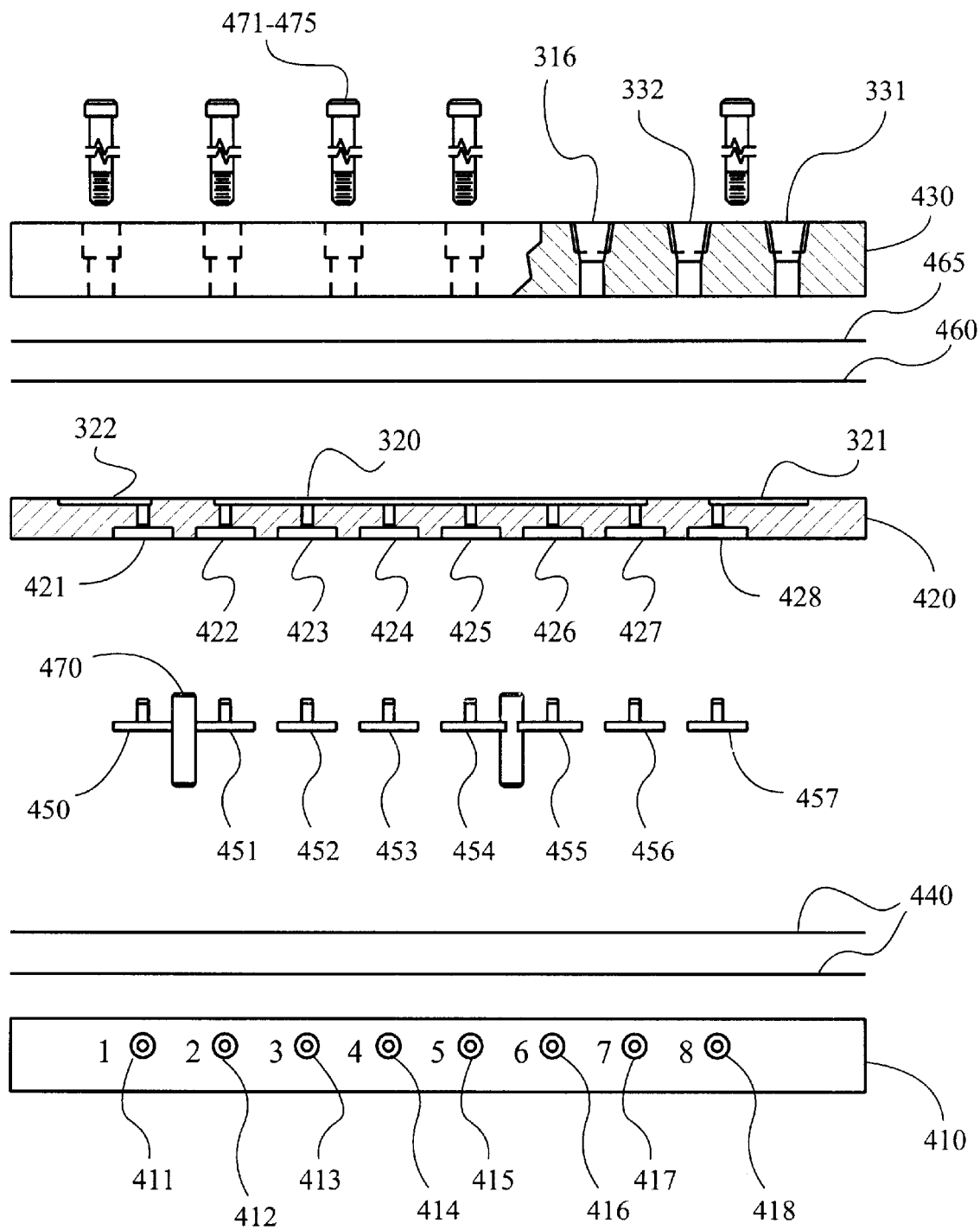
FIG. 4 is an exploded side view of the embodiment of FIG. 3.

Referring now to FIG. 4, a side exploded view of the stream switching portion 391 is shown. In this embodiment, the stream switching portion constitutes upper, middle, and lower plates aligned and connected together by dowel pins 470 and torque screws 471–475. The lower plate, referred to as a manifold plate 410, includes eight actuation ports 411–418 connected by tubing to solenoids 350–357 (not explicitly shown in FIG. 4). The middle plate, also called a piston plate 420, includes eight locations 421–428 designed to receive respective pistons 450–457. Middle plate 420 also includes shallow channels, chambers, or grooves that form areas 320–322, as described with reference to FIG. 3. The upper plate, referred to as the primary plate 430, includes screw holes corresponding to the torque screws, as well as three exemplary fluid ports 316, 332, and 331. Eight pistons 450–457 (corresponding to ports 311–316, 332–333) as well as a pair of actuating diaphragms 440 lie between manifold plate 410 and middle plate 420. Sealing diaphragm 465 and cushion diaphragm 460 lie between the primary plate 430 and middle plate 420. These diaphragms ensure a leak-free fit between each pair of plates and between a piston and its corresponding port. The actuating diaphragms may be made from Kapton of about 3 mm thickness. Similarly, the sealing diaphragms may be made from Teflon coated Kapton. However, as would be appreciated by those of ordinary skill, the invention is not limited solely to these sealing diaphragms.

Figure 5:
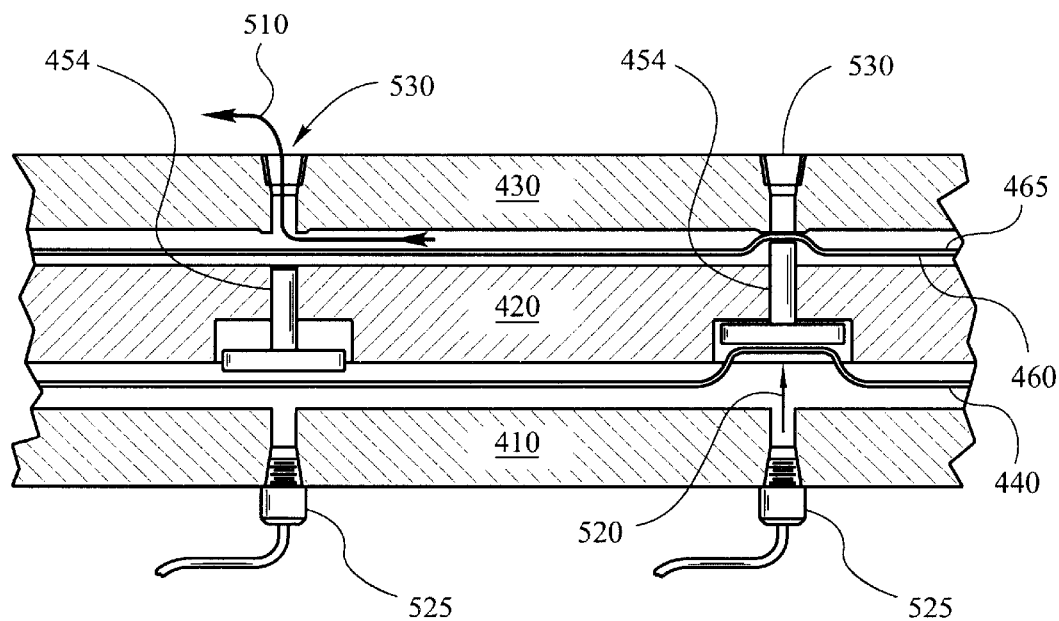
FIG. 5 is a magnified view of FIG. 4.

FIG. 5 includes a close-up view of piston 454, manifold plate 410 with attached solenoid or other appropriate fluid flow activation switch, middle plate 420, primary plate 430 including passage 530 (corresponding to one of the ports illustrated in FIGS. 3 and 4), and diaphragms 440, 460, and 465. The left portion of FIG. 5 includes a fluid stream 510 such as a calibration gas or fluid sample. The right portion of FIG. 5 includes actuation gas 520. When a port is open (as shown on the left side of FIG. 5), a fluid stream 510 between primary plate 430 and diaphragm 465 exits through passage 530. Conversely, when a port is closed (as shown on the right), there is no flow of a fluid stream 510. Instead, an actuation gas 520 is applied by the solenoid 525 against the piston head of piston 454. The piston 454 is forced upward, with its narrow end abutting the lower end of passage 530 formed in primary plate 430. Because the relatively large surface area of its head is presented to the actuating fluid 520, the piston 454 inherently multiplies the force available such that a gas tight seal is formed against the passage 530. As can be appreciated, a piston is not the only possible actuation member, with suitable devices including solenoids, flapper valves, direct diaphragm valves, and others.

Referring to FIGS. 3, a sample from stream 1 302 will be used to illustrate the operation of the device. The pressure in each stream from a pipeline is normally reduced to about 15–25 psi. Consequently, a sample from, for example, a process pipeline travels to channel 320 via port 312 when port 312 is open. Port 312 being open corresponds to piston 454 being in a lower position. As can be understood from FIG. 4 and as is shown in FIG. 5, the piston 454 is forced to this lower position from the fluid pressure applied through stream 1 302 and a lack of actuation pressure applied by solenoid 354. Gravity may also assist in the piston falling to a lower position. To avoid cross-contamination, when port 312 is open, ports 311, 313, and 314 are, therefore, closed in normal operation. This closure of ports 311, 313, and 314 corresponds to pistons 455, 453 and 452 being in an elevated position by activation fluid pressure applied through solenoids 355, 353 and 352. As can consequently be appreciated, the assembly shown in FIG. 4 need not be vertical, but instead can operate from a variety of angles, and the use of terms such as "lower" and "upper" is merely for explanatory purposes.

The fluid sample travels through port 312 and along common stream channel 320 to blocking port 315, which is also open by operation of the associated solenoid. The sample then travels through blocking port 315 and along gas path 342 that includes a "T" at point 343. This "T" intersection at point 343 splits the sample into two portions. A first portion travels to sample shut off channel 321 via actuatable port 332. When port 332 is open, the sample travels along the sample shut off channel to port 331, which then allows this first portion of the sample to flow out channel 1 340 to a first gas chromatograph (not shown). A second portion of the sample travels to sample shut off channel 322 via an open actuatable port 333. Port 334 allows this second portion of the sample to flow out channel 2 345 to a second gas chromatograph (not shown). As would be appreciated by one of ordinary skill in the art, gas path 342 may be external tubing or may be milled into one or more plates, such as lines permanently drilled into primary plate 430.

The double block and double bleed design of this embodiment has particular advantages. For example, when switching from stream 1 to stream 2, the system must be bled. First, the sample shut offs are closed to block the flow stream by the closure of sample shut off ports 332 and 333 by actuation of solenoids 350 and 357. Stream port 312 is also closed to block the flow of pressurized gas from stream 1. A short time thereafter, sample bleed port 316 in the common stream path is opened while port 315 is still open, allowing the pressurized gas in common stream path 320 to equalize to atmospheric pressure. Simultaneously, inside the associated gas chromatograph 150, the carrier gas associated with the well-known operation of the chromatographic valve sampling injects an aliquot of sample fluid for analysis by the gas chromatograph. When this occurs, the remaining fluid in the system downstream of the sample shut offs is allowed to equalize to atmospheric pressure. At that time, the sample shut offs can be opened, the sample bleed port 316 closed, and the system purged with the new stream from stream 2. Because the pressure of the stream switching system has already been lowered to atmospheric pressure, and because stream 2 is under pressure, the sample from stream 2 will quickly flow through the stream switching system. This results in a faster purging with lower volumes of the new sample being necessary.

As an additional benefit to this embodiment, the use of two channels allow near-parallel analysis by separate gas chromatographs or detectors within the same gas chromatograph, which can speed the sample analysis of a complex sample having numerous components. For example, an open first sample shut off and closed second sample shut off allows sample to flow through channel 1 for a period of five seconds. An open second sample shut off and closed first shut off could them allow sample to flow through channel 2 for the next five seconds. This results in near-simultaneous analysis by the gas chromatographs or detectors.

Moreover, this design is particularly desirable because the advantages recited above are achieved without the expense otherwise necessary (such as for extra valves, etc) to attain a double block and double bleed configuration. Further, the above design can be easily modified for particular situations. For example, additional ports can be freed for use as stream ports if only single blocking or only a single channel is desired. The design can also be modified to be a single bleed design, if desired. The design may also be modified to add or subtract parts as necessary.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. For example, the disclosed stream switching systems may connected to a variety of associated instruments, such as a gas chromatograph, a mass spectrometer, a moisture analyzer, or an infrared analyzer. Accordingly, the scope of protection is not limited to the embodiments described herein, but is only limited by the claims that follow, the scope of which shall include all equivalents of the subject matter of the claims.

What is claimed is:

1. A stream switching system, comprising:
   a housing forming at least one common stream channel portion, said common stream channel portion including a first actuatable input port corresponding to a first fluid sample, a second actuatable input port corresponding to a second fluid sample, a first actuatable output port to direct said first and second fluid samples away from said common stream channel portion, and a second actuatable output directly connected to vent a fluid sample from said housing to atmosphere said first actuatable input port, second actuatable input port and first actuatable output port, and second actuatable output port each being actuatable between an open position to allow the flow of fluid and a closed position to prevent the flow of fluid.

2. The stream switching system of claim 1, further comprising:
   a first sample shut off portion having a third input port and a second output port, wherein at least one of said third input port and said second output port being actuatable, said shut off portion being connected to said output part of said common stream path with said common stream channel and wherein said housing forms said first sample shut off portion.

3. The stream switching system of claim 1, wherein said common stream channel portion further includes a second actuatable output, said second actuatable output being directly connected to vent a fluid sample from said housing.

4. The stream switching system of claim 1, wherein said open and closed positions of said first actuatable input port are controlled by a first activation member within said housing, said actuation member being movable between a first position and a second position, said first actuatable input allowing a flow of said first fluid sample through said first input when said first actuation member is in said first position and said first actuatable input not allowing said flow of said first fluid sample through said first input when said first actuation member is in said second position.

5. The stream switching system of claim 4, wherein said actuation member is a piston.

6. The stream switching system of claim 4, further comprising:
   a respective piston for each of said actuatable inputs and actuatable outputs of said common stream path portion.

7. The stream switching system of claim 4, wherein said first piston is placed in said second position by use of a first gas flow actuation switch attached to said housing.

8. The stream switching system of claim 7, wherein said first gas flow actuation switch is a solenoid.

9. The stream switching system of claim 1 wherein said housing comprises a plurality of layers, each pair of said plurality of layers being separated by one or more diaphragms.

10. The stream switching system of claim 2, said housing further comprising
    second sample shut off portion being connected to said output port of said common stream path with said common stream channel portion.

11. The stream switching system of claim 1, wherein said common stream channel portion is a chamber in said housing.

12. The stream switching system of claim 2, wherein said housing is comprised of a plurality of adjacent attachable components, said common stream channel portion and said sample shut off portion being chambers formed by more than one of said plurality of adjacent attachable components.

13. The stream switching system of claim 1, wherein said housing comprises a primary plate, a middle plate and a manifold plate, said common stream path channel being formed at an interface between said middle plate and said primary plate.

14. The stream switching system of claim 1, further comprising a plurality of gas flow actuation switches attached to said housing.

15. The stream switching system of claim 1, further comprising a plurality of gas flow actuation switches not attached to said housing.

16. A stream switching system suitable for connection to at least one fluid measurement device, comprising:
    a first fluid sample source corresponding to a first fluid sample, said first fluid sample not being of a calibration fluid;
    a second fluid sample source corresponding to a second fluid sample, said second fluid sample not being of a calibration fluid;
    a third fluid sample source corresponding to a calibration fluid sample of known composition;
    a common flow apparatus including a first input port corresponding to said first fluid sample source, a second input port corresponding to said second fluid sample source, a third input port corresponding to said third fluid sample source, a first output port, a second output port and a common flow area connected to said first, second, and third inputs and said first output, each of said first, second, and third inputs and said first output being distinct from one another, said first output port being connected serially to, and upstream of, said second output port and said second output port being suitable for connection to and upstream of said fluid measurement device.

17. The stream switching system of claim 16, further comprising:
    a third output port, said third output port corresponding to a first bleed path said third output port being connected to said common flow area.

18. The stream switching system of claim 16, wherein said first, second and third input ports, said first output port and said common flow area are elements of a single gas-tight housing.

19. The stream switching system of claim 18, wherein said single gas-tight housing also contains at least one sample shut off area suitable to prevent the flow of gas sample.

20. The stream switching system of claim 18, wherein said single gas-tight housing contains a plurality of movable members that selectively open and close said first, second, and third input ports.

21. The stream switching system of claim 16, wherein said first output port connects to a fluid conduit suitable to direct the flow of a fluid sample, said fluid conduit containing a bifurcation point that divides said fluid conduit into multiple flow channels.

22. The stream switching system of claim 16, wherein said output port is switchable between an open and closed position, said open position allowing the flow of a fluid sample through said output port and said closed position not allowing the flow of said fluid sample through said output port.

23. The stream switching system of claim 1, wherein said first and second actuatable input ports, and said first actuatable output port are within said housing.

24. The stream switching system of claim 1, wherein said first actuatable input port corresponds to a first fluid flow switching point inside said housing, said second actuatable input port corresponds to a second fluid flow switching point inside said housing, and said first actuatable output port corresponds to a third fluid flow switching point inside said housing.

25. The stream switching system of claim 16, wherein said common flow apparatus comprises a common flow channel and a separate sample shut off channel, said common flow channel including at least said first, second and third input ports and said first output port, and said separate sample shut off channel including at least said second output port, said common flow channel and said sample shut off channel each being part of said common flow apparatus.

26. The stream switching system of claim 25, said common flow channel further comprising a third output port not connected to a fluid measurement device.

27. The stream switching system of claim 26, said third output port venting fluid sample to atmosphere.

28. The stream switching device of claim 16, wherein said second output port is a gas chromatograph.

29. The stream switching device of claim 16, wherein each of said first, second, and third input ports and said first and second output ports are independently actuatable between an open position and a closed position to allow or prevent the flow of fluid.

30. The stream switching system of claim 17, wherein each of said first, second, and third input ports and said first, second, and third output ports are individually actuatable between an open position and a closed position.

31. The stream switching system of claim 16, wherein said stream switching system connects to two or more gas chromatographs.

32. The stream switching system of claim 16, wherein said stream switching system connects to two or more sample valves.

33. The stream switching system of claim 1, further comprising first, second, and third solenoids attached to said housing and corresponding to said first and second actuatable input ports and said actuatable output port.

34. The stream switching system of claim 16, further comprising first, second, and third solenoids attached to said housing and corresponding to said first second and third input ports and said first output port.

35. A stream switching system for connection to a gas chromatograph, comprising:
  a housing defining a common stream channel, a first sample shut off channel, said common stream channel connected to first and second fluid sources and an output port, wherein said common stream channel has a first fluid flow control location corresponding to said first fluid source, and a second fluid flow control location corresponding to said second fluid source said first and second fluid flow control locations being inside said housing and wherein said first sample shut off channel includes a first input port and a first output port, said first input port being connected to said output port of said common stream channel and said output port and said first sample shut off being connected to a first gas chromatograph;
  a first valve member inside said housing, said first valve member movable between an open and closed position and corresponding to said first fluid flow control location;
  a second valve member inside said housing, said second valve member movable between an open and closed position and corresponding to said second fluid flow control location;
  a first switch external to said housing to selectively provide a first actuation gas to said first valve member to move said first valve member from said open to said closed position;
  a second switch external to said housing to selectively provide a second actuation gas to said second valve member to move said second valve member from said open to said closed position.

36. The stream switching system of claim 35, wherein said first valve member is a piston.

37. The stream switching system of claim 35, wherein said first switch is a solenoid.

38. The stream switching system of claim 35, further comprising:
  an output port inside said housing and as part of said common stream channel.

39. The stream switching system of claim 38, further comprising:
  a first sample shut off channel defined by said housing and separate from said common stream channel, said first sample shut off channel including a first input port and a first output port, said input port being connected to said output port of said common stream channel and said output port of said first sample shut off being connected to a first sample valve.

* * * * *